US012619966B2

(12) United States Patent
Austring et al.

(10) Patent No.: US 12,619,966 B2
(45) Date of Patent: May 5, 2026

(54) SYSTEM AND METHOD FOR DATA PROVIDER TRACKING AND MONETIZATION

(71) Applicant: Synerio Technologies, Inc., Fort Worth, TX (US)

(72) Inventors: Ronald R. Austring, English Harbour (AG); Kenneth A. Hill, Sr., Fort Worth, TX (US)

(73) Assignee: Technologies IP, LLC, Fort Worth, TX (US)

( * ) Notice: Subject to any disclaimer, the term of this patent is extended or adjusted under 35 U.S.C. 154(b) by 852 days.

(21) Appl. No.: 17/105,097

(22) Filed: Nov. 25, 2020

(65) Prior Publication Data

US 2022/0092566 A1     Mar. 24, 2022

Related U.S. Application Data

(60) Provisional application No. 63/110,807, filed on Nov. 6, 2020, provisional application No. 63/080,412, filed on Sep. 18, 2020.

(51) Int. Cl.
*G06Q 20/12*        (2012.01)
*G06F 16/22*        (2019.01)
(Continued)

(52) U.S. Cl.
CPC ......... *G06Q 20/1235* (2013.01); *G06F 16/22* (2019.01); *G16H 10/60* (2018.01);
(Continued)

(58) Field of Classification Search
CPC .......... G06Q 20/1235; G06Q 20/0655; G06Q 20/367; G06Q 40/04; G06Q 2220/12; G16H 40/20; G16H 10/60; G06F 16/22
See application file for complete search history.

(56) References Cited

U.S. PATENT DOCUMENTS 6,163,801 A      12/2000 O'Donnell et al.
10,860,604 B1 * 12/2020 Pandey ............... G06F 11/1402
(Continued)

FOREIGN PATENT DOCUMENTS

WO        2020077352 A1      4/2020

OTHER PUBLICATIONS

International Search Report; Application No. PCT/US20/062250; Feb. 17, 2020.

(Continued)

*Primary Examiner* — Steven G.S. Sanghera
(74) *Attorney, Agent, or Firm* — Whitaker Chalk Swindle & Schwartz PLLC; Enrique Sanchez, Jr.; Juan Vasquez

(57)        ABSTRACT

A data provider tracking and monetization system is disclosed that can provide data aggregation infrastructure, tracking, and monetization. The present disclosure achieves the technological advantage of organizing data that is received from multiple data providers for a single person to provide any missing data. The data providers can be tracked via the provision of their data, such that they can be incentivized for providing the data. The present disclosure improves traditional systems by generating a data structure that includes metadata to identify data providers and data requestors to minimize network congestion, uncategorized data, and stale data that ravages traditional systems. Further by publishing the transactions on a distributed ledger, such as a blockchain, the request for data and all of the contributions thereto provide an open, verifiable, and immutable record of the transaction.

20 Claims, 5 Drawing Sheets

(51) Int. Cl.

| | |
|---|---|
| *G06Q 20/06* | (2012.01) |
| *G06Q 20/36* | (2012.01) |
| *G06Q 40/04* | (2012.01) |
| *G16H 10/60* | (2018.01) |
| *G16H 40/20* | (2018.01) |

(52) U.S. Cl.

CPC ......... *G16H 40/20* (2018.01); *G06Q 20/0655* (2013.01); *G06Q 20/367* (2013.01); *G06Q 40/04* (2013.01); *G06Q 2220/12* (2013.01)

(56) References Cited

U.S. PATENT DOCUMENTS

| | | | |
|---|---|---|---|
| 10,860,741 | B1 | 12/2020 | Liu |
| 2007/0078684 | A1 | 4/2007 | Dettinger et al. |
| 2007/0078685 | A1 | 4/2007 | Dettinger et al. |
| 2008/0046292 | A1 | 2/2008 | Myers et al. |
| 2008/0319942 | A1 | 12/2008 | Courdy et al. |
| 2013/0159017 | A1 | 6/2013 | Burkholder |
| 2014/0136237 | A1* | 5/2014 | Anderson .............. G16H 10/60 |
| | | | 705/3 |
| 2016/0004820 | A1 | 1/2016 | Moore |
| 2017/0161435 | A1 | 6/2017 | Orosco et al. |
| 2018/0075091 | A1 | 3/2018 | Weiss et al. |
| 2019/0188760 | A1* | 6/2019 | Ekambaram ....... G06Q 30/0283 |
| 2019/0354693 | A1 | 11/2019 | Yoon et al. |
| 2020/0012676 | A1 | 1/2020 | Narang et al. |
| 2020/0168307 | A1 | 5/2020 | Chen et al. |
| 2020/0227160 | A1 | 7/2020 | Youngblood et al. |
| 2020/0320006 | A1 | 10/2020 | Heremagalur Ramaprasad et al. |
| 2020/0334032 | A1* | 10/2020 | Smith ..................... G06F 21/64 |
| 2020/0394171 | A1 | 12/2020 | Coker |
| 2021/0209145 | A1 | 7/2021 | Oliner |
| 2022/0019366 | A1* | 1/2022 | Freilich .............. G06F 21/6218 |

OTHER PUBLICATIONS

International Search Report; Application No. PCT/US20/62364; Feb. 23, 2020.

PCT International Patent Appl. No. PCT/US22/26593, filing date Apr. 27, 2022, International Search Report and Written Opinion dated Aug. 26, 2022, 12 pages.

* cited by examiner

FIG. 2

SYSTEM AND METHOD FOR DATA PROVIDER TRACKING AND MONETIZATION

CROSS REFERENCE TO RELATED APPLICATIONS

The present application claims priority to U.S. Provisional Application Ser. No. 63/080,412, filed on Sep. 18, 2020, entitled "PATIENT DATA PROVISION, CONSUMPTION, AND ROYALTY PROCESSING SYSTEM," and U.S. Provisional Application Ser. No. 63/110,807, filed on Nov. 6, 2020, entitled "DATA PROVIDER TRACKING AND MONETIZATION SYSTEM," the entirety of both provisional applications is incorporated herein by reference.

TECHNICAL FIELD

The present disclosure generally relates to patient data processing systems, and more specifically to patient data processing systems configured to track data and exchange currency between multiple entities.

BACKGROUND

Numerous healthcare providers participate in each phase of care. Healthcare service providers, including pharmacies, physicians, hospitals, laboratories, clinics, medical institutions, and regulatory agencies that develop clinical standards of care, historically have operated their own data systems, typically according to unique and different formats and processes.

A network of three database components aggregate and maintain patient data from a plurality of sources. The three database components include a structured healthcare database called electronic patient outcome data ("EPO data"); an electronic pharmacy record ("ePR") database; and an electronic patient outcome record ("EPOR") database that is populated by data from the EPO data and ePR databases.

A patient's private information, including the patient's name, address, phone number, social security number, insurance information, medical history, clinical information, and other relevant information, can be stored in an Electronic Health Record (EHR) database, such as an Electronic Patient Outcome Record (EPOR), Solid POD, XML, file, or other suitable data storage element.

Often times a "complete" picture of a patient is not realizable due to different "holes" in a patient's EPO data. These holes exist because typically, each generator of patient data specializes in only its particular area and has no means to consume and provided data from other generator of patient data for a particular patient. No data structure has been proffered to handle all of the disparate data generated by various data generators for a patient. Even more difficult would be to incorporate non-healthcare data in an attempt to generate a "complete" picture of a person that extends beyond a patient. Further, there has been no incentive for patient data generators to share their data with others. The sharing of data has an inherent cost associated with the maintenance and transfer of that data. With tightening budgets and diminishing support, even in-person requests for medical records can take months to acquire.

SUMMARY

The present disclosure achieves technical advantages as a data provider tracking and monetization systems adapted to provide data aggregation infrastructure, tracking, and monetization.

The present disclosure achieves the technological advantage of organizing data that is received from multiple data providers for a single person to provide any missing data. The data providers can be tracked via the provision of their data, such that they can be incentivized for providing the data. The present disclosure improves traditional systems by generating a data structure that includes metadata to identify data providers and data requestors to minimize network congestion, uncategorized data, and stale data that ravages traditional systems. Further by publishing the transactions on a distributed ledger, such as a blockchain, the request for data and all of the contributions thereto provide an open, verifiable, and immutable record of the transaction. Such record can be easily audited to ensure compliance with various laws and regulations.

In particular, the present disclosure improves the performance of traditional systems by facilitating settlement between the data-consumer and the data-provider that can result in the exchange of a digital currency (Bitcoin SV), cryptocurrency (e.g., Bitcoin®, etc.), utility tokens (e.g., EHRCash™) vouchers, wire transfers, ACH transactions, or other suitable currency, between the parties involved in the patient data request and provisioning. The present disclosure can eliminate the need for standard accounting processes (e.g., invoicing, statements, accounts receivable and accounts payable) in order to transfer money between data exchange partners. Advantageously, the present disclosure advances the state of the art by providing various algorithms implemented by one or more processors that can calculate fixed and variable royalties based upon data category, data size, request attributes, or other relevant thresholds or metrics. The present disclosure can implement an EHR data blockchain system (including an EHR Data API and an EHR transaction blockchain) that can provide a centralized patient data processing location that creates transparency, immutable verification, interactive record editing, and cryptocurrency transactions. The EHR Data API can access and retrieve patient records and generate metadata to rectify errors in a patient's record. An addressable attribute can be any attribute that can be referenced by the system via an address. For example, any data item can be addressed using an ASCII string that can define the location of the data. The string can be a Uniform Resource Identifier (URI), or other suitable mechanism. Any exemplary URI can be request-.patient.name.

In one exemplary embodiment, when a PUT operation is performed: an instance-node can be created, if one does not already exist for the UUID specified by the data-provider; a new version-node can be created; the version-id, supplied by the data-provider, can be stored in the version-node as an attribute; the data-provider-id can be stored in the version-node as an attribute; and a property-operation can be created, for each data-item within the PUT operation as it relates to all previous version-node(s) of the instance-node.

BRIEF DESCRIPTION OF THE DRAWINGS

FIG. 2 illustrates a schematic view of a node hierarchy of a Global Person Record, in accordance with one or more exemplary embodiments of the present disclosure;

DETAILED DESCRIPTION OF THE INVENTION

The preferred version of the disclosure presented in the following written description and the various features and advantageous details thereof, are explained more fully with reference to the non-limiting examples included in the accompanying drawings and as detailed in the description, which follows. Descriptions of well-known components have been omitted so to not unnecessarily obscure the principle features described herein. The examples used in the following description are intended to facilitate an understanding of the ways in which the disclosure can be implemented and practiced. Accordingly, these examples should not be construed as limiting the scope of the claims.

Figure 1:
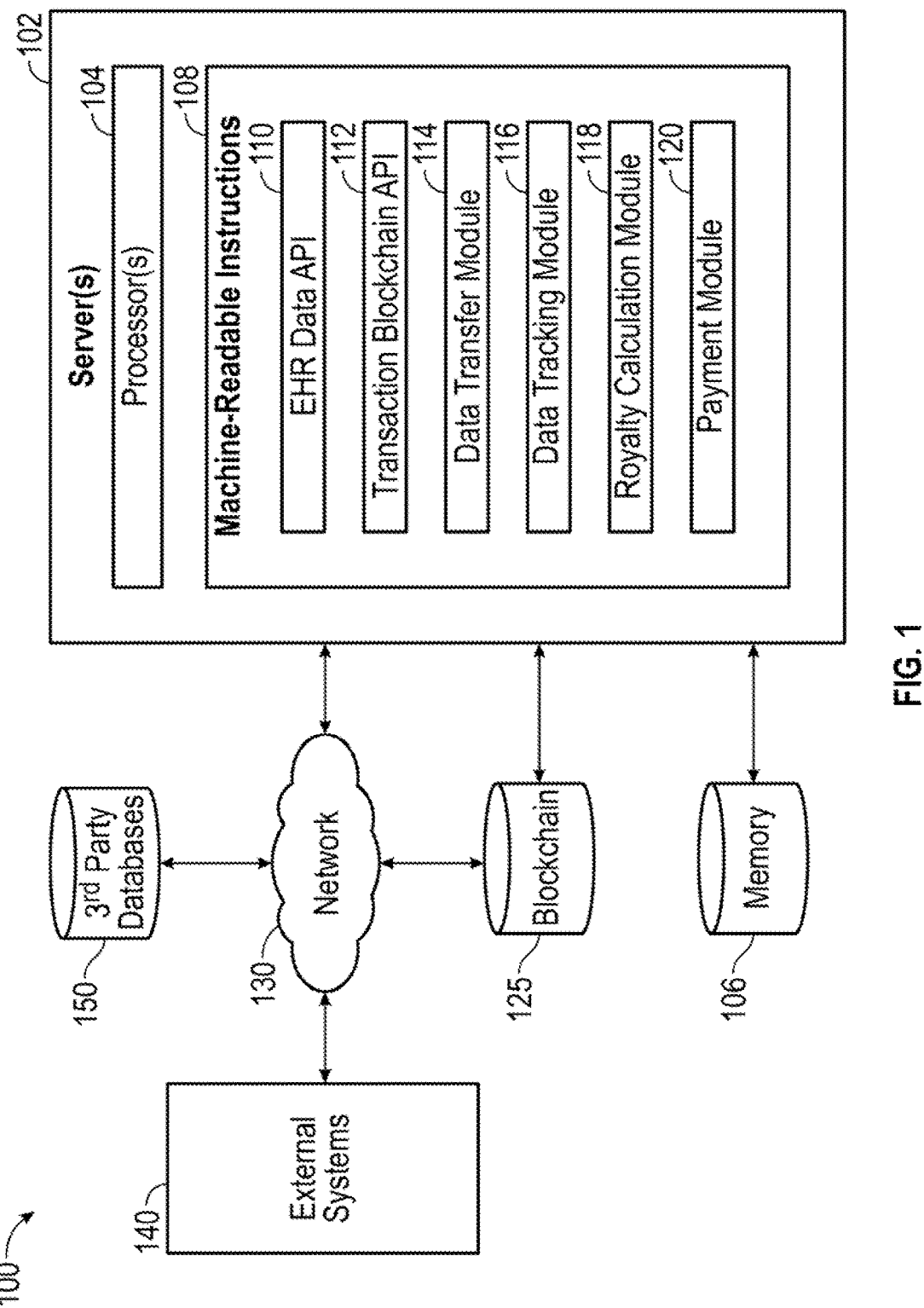
FIG. 1 illustrates a schematic view of an EHR data utility system, in accordance with one or more exemplary embodiments of the present disclosure.

FIG. 1 illustrates an Electronic Health Record (EHR) data utility system 100, in accordance with one or more exemplary embodiments of the present disclosure. The EHR-Data-Utility system 100 can include a server 102, third-party databases 150, a distributed ledger 125, a network 130, and external systems 140.

The server 102 can include one or more processors (or cores) 104, a memory 106, and machine-readable instructions 108. In one exemplary embodiment, the machine-readable instructions 108 can include an EHR Data API 110, a transaction blockchain API 112, a data transfer module 114, a data tracking module 116, a royalty calculation module 118, and a payment module 120. In another exemplary embodiment, the server 102 can host an EHR Data Portal that can provide a DP or DC user (e.g., Physician, Manufacturer, Pharmacy, or other relevant entity) with access to the system 100 after an authenticated login. In one exemplary embodiment, the EHR Data Portal can be achieved via software, hardware, an application programming interface (API), a network connection, a network transfer protocol, HTML, DHTML, JavaScript, Dojo, Ruby, Rails, other suitable applications, or suitable combinations thereof. In another exemplary embodiment, the EHR Data Portal can allow a Data Consumer (DC) or a Data Provider (DP) to submit or respond to data requests via a user interface, automatic script execution, or other suitable mechanism. In another exemplary embodiment, the EHR Data Portal can maintain a DP or DC's tokens and/or financial information.

The server 102 can be implemented in hardware, software, or a suitable combination of hardware and software therefor, and may comprise one or more software systems operating on one or more servers, having one or more processors, with access to memory. Server(s) can include electronic storage, one or more processors, and/or other components. Server(s) can include communication lines, or ports to enable the exchange of information with a network and/or other computing platforms. Server(s) can also include a plurality of hardware, software, and/or firmware components operating together to provide the functionality attributed herein to server(s). For example, server(s) can be implemented by a cloud of computing platforms operating together as server(s). Additionally, the server can include memory 106.

Server(s) can include electronic storage, one or more processors, and/or other components. Server(s) can include communication lines, or ports to enable the exchange of information with a network and/or other computing platforms. Server(s) can also include a plurality of hardware, software, and/or firmware components operating together to provide the functionality attributed herein to server(s). For example, server(s) can be implemented by a cloud of computing platforms operating together as server(s).

Memory 106 can comprise electronic storage that can include non-transitory storage media that electronically stores information. The electronic storage media of electronic storage may include one or both of system storage that can be provided integrally (i.e., substantially non-removable) with server(s) and/or removable storage that can be removably connectable to server(s) via, for example, a port (e.g., a USB port, a firewire port, etc.) or a drive (e.g., a disk drive, etc.). Electronic storage may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage can include one or more virtual storage resources (e.g., cloud storage, a virtual private network, and/or other virtual storage resources). Electronic storage can store machine-readable instructions, software algorithms, information determined by processor(s), information received from server(s), information received from computing platform(s), and/or other information that enables server(s) to function as described herein. The electronic storage can also be accessible via a network connection.

Processor(s) 104 can be configured to provide information processing capabilities in server(s). As such, processor(s) can include one or more of a digital processor, an analog processor, a digital circuit designed to process information, an analog circuit designed to process information, a state machine, and/or other mechanisms for electronically processing information, such as FPGAs or ASICs. The processor(s) can be a single entity or include a plurality of processing units. These processing units can be physically located within the same device or represent the processing functionality of a plurality of devices operating in coordination or software functionality.

The processor(s) 104 can be configured to execute machine-readable instructions 108 or learning modules by software, hardware, firmware, some combination of software, hardware, firmware, and/or other mechanisms for configuring processing capabilities on processor(s). As used herein, the term "machine-readable instruction" may refer to any component or set of components that perform the functionality attributed to the machine-readable instruction component. This can include one or more physical processors during execution of processor readable instructions, the processor readable instructions, circuitry, hardware, storage media, or any other components.

The server 102 can be configured with machine-readable instructions 108 having one or more functional modules. The machine-readable instructions can be implemented on one or more servers, having one or more processors, with access to memory. The machine-readable instructions can be a single networked node, or a machine cluster, which can include a distributed architecture of a plurality of networked nodes. The machine-readable instructions can include control logic for implementing various functionality, as described in more detail below. The machine-readable instructions can include certain functionality associated with an EHR Data Portal, EHR Data API 110, EHR transaction blockchain API 112, a data transfer module 114, a data tracking module 116, a royalty calculation module 118, and payment module 120. External databases 106 and external systems 140, as well as an EHR Data Blockchain client, can also be implemented on one or more servers 102, having one or more processors 104, with access to memory 106.

Third-party databases 150 can be operably coupled to the system components via the network 130. In one exemplary embodiment, the third-party databases 150 can include an electronic medical record system (EMR), an Electronic Patient Outcome Record (EPOR) database, pharmacy databases, a plurality of patient databases, a clinical database, a genomic database, a laboratory database, a disease database, a standardized drug database, a research database, and other suitable databases. In another exemplary embodiment, the third-party databases can function as archival nodes. The archival nodes can keep a real-time (sub-millisecond) encrypted copy of the distributed ledger 125. The archival node can provide fault tolerance and makes the contents of the distributed ledger 125 readily available to a host so that additional data processing, reporting, and analytics can be achieved. Instead of having to traverse the EHR Data API 110, the host can query its own machines to acquire the data. Any third party can host a drug archival node. In another exemplary embodiment, the archival node can provide data restoration to the distributed ledger 125. In another exemplary embodiment, the archival node can keep the older distributed ledger data accessible in a non-production system, so that the production distributed ledger can direct its full capabilities toward current transactions. In another exemplary embodiment, the distributed ledger can be transferred to the archival node once a distributed ledger transaction closes.

In one exemplary embodiment, the EHR Data API 110 can provide an interface that defines interactions between multiple software components. For example, EHR Data API 110 can define the kinds of calls or requests that can be made, how to make them, the data formats that should be used, the conventions to follow, and other suitable functionality. In another exemplary embodiment, the EHR Data API 110 can access and retrieve patient identifiable information (PII) and generate a non-patient-identifiable Single Purpose Patient ID (SPPID) for a particular patient, as well as timestamps. In operation, the EHR Data API 110 allows the system to interact with electronic patient records. For example, the EHR Data API 110 can allow data to be read and written to one or more databases (e.g., GPR, EPO, third-party, or other suitable databases), among other relevant functions.

In one exemplary embodiment, the EHR transaction blockchain API 112 can provide an interface that defines interactions between multiple software components. For example, EHR transaction blockchain API 112 can define the kinds of calls or requests that can be made, how to make them, the data formats that should be used, the conventions to follow, and other suitable functionality. In another exemplary embodiment, the transaction blockchain API 112 can be configured to store the timestamp, as well as particular, discrete data retrieved from the GPR for a patient, execute smart contracts, and control the execution of cryptocurrency transfers, among other functions. In operation, the transaction blockchain API 112 allows the system to interact with the blockchain. For example, the transaction blockchain API 112 can allow data to be written to the blockchain and can execute smart contracts related thereto, among other relevant functions.

In one exemplary embodiment, a data transfer module 114 can transmit and receive data to and from an external system 140, memory 106, or third-party database 150 via the server 102. In one exemplary embodiment, the data transfer module 114 can be used to PUT and GET data to/from one or more databases (e.g., GPR, EPO, third-party, or other suitable databases). In another exemplary embodiment, the data transfer module 114 can implement instantiate the EHR Data API 110 to assist in the data transfer. When the data transfer module 114 is used to retrieve data, the operation is known as a GET operation. For large data items (e.g., videos, images, etc.), the data transfer module 114 can transfer data to the external system 140. For example, the data transfer module 114 can move, copy, or stream data to the external system 140. In another exemplary embodiment, the data transfer module 114 can use a PUT operation to insert data into one or more databases (e.g., GPR, EPO, third-party, or other suitable databases). In another exemplary embodiment, during a PUT operation, the app-id, and data-provider-id can be used by the data transfer module 114 when processing a request. In another exemplary embodiment a query, having fields, parameters, or other relevant data can be transferred by the data transfer module 114. The data transfer module 114 can append metadata to the data transfer. For example, the metadata can include a unique identifier for a session, a token, a unique identifier for the DC, a timestamp, or other relevant data.

In one exemplary embodiment, a data tracking module 116 can append metadata identifying the origin of the data to data transferred via the server 102. In another exemplary embodiment, since a variety of data-providers can contribute to specific instances of data within the GPR, the data tracking module 116 can track the data contributions by writing the property-operations and the data-provider-id to the GPR. Creation of, and changes to, the property-collection can be made by a collection of property-operations that can be tracked by data tracking module 116. These property-operations, along with the provider-id of the data-provider can be stored in a time stamped version-node in memory 106.

In one exemplary embodiment, a royalty calculation module 118 can analyze the data transfers and determine the proper royalty for each data request transaction. The royalty calculation module 118 can perform royalty-operation qualification, which can return a result set of royalty-operations. In another exemplary embodiment, a royalty calculation module 118 can calculate a royalty for each provider-id in a property-operations-result-set, as discussed in more detail below. The royalty calculation module 118 can determine which royalty-operations qualify based on: configuration settings, request message contents, connection properties, app-id, provider-id, any addressable attribute, etc. In another exemplary embodiment, the royalty calculation module 118 can calculate a royalty for the parties (e.g., person, data-providers, ehr-data-utility provider, etc.) involved in a GET or PUT operation.

In another exemplary embodiment, a royalty percentage of a specific amount can be determined by the royalty calculation module 118 for the patient data. In another exemplary embodiment, a flat-fee processing fee can be determined for all parties involved in a query transaction. The specific royalty amount can be determined by the royalty calculation module 118 based upon the cost of the service, cost of the data transfer, or other relevant metric. The royalty calculation module 118 can divide the royalty amount amongst the participating parties (including the patient), such that the DPs, the patient, and the utility provider each can receive a percentage of the royalty, such that each party related to the transaction gets rewarded. In another exemplary embodiment, when a DP submits data to the Utility, the royalty calculation module 118 can generate and append metadata to the data to identify the DP, the patient (using a temporary patient identifier), and a time-stamp, among other relevant data.

In one exemplary embodiment, the payment module 120 can determine if a smart contract was utilized during prescription filling and may result in the exchange of crypto-currency (e.g., EHRCash™, Bitcoin®, etc.), utility tokens, vouchers, or other suitable notes, between the parties involved in the smart contract. For example, the exchange of EHRCash™ tokens can be immediate (sub-millisecond delay) and can eliminate the need for standard accounting processes (e.g., invoicing, statements, accounts receivable and accounts payable) in order to collect money from trading partners. In another exemplary embodiment, the payment module 120 can utilize stored wallet information to effect the cryptocurrency transactions. The modules described herein can be executed, called, or otherwise implemented via server, control logic, API, or other suitable means.

The distributed ledger 125 can be an EHR Data block-chain implemented on one or more platforms, including BigChainDB, nChain, Ethereum, Hyperledger, R3, Ripple, EOS, or other suitable blockchain platform. The EHR Data blockchain can be a public blockchain, accessible to the general public, or a private blockchain, accessible only by those parties credentialed for access.

External systems 140 can be operably coupled to the system components via the network 130. External systems 140 can include patient devices, pharmacy devices, payer devices, financial institution devices, insurance devices, or other suitable systems or devices. Such systems and devices can include smart phones, tablets, wearable devices, laptops, desktops, servers, appliances, or other suitable devices. In one exemplary embodiment, an external system 140 can be a mobile device connected to the network 130.

The aforementioned system components, APIs, and modules can be communicably coupled to each other via the Internet, intranet, system bus, or other suitable network 130. The communication can be encrypted, unencrypted, over a VPN tunnel, or other suitable communication means. The network 130 can be a WAN, LAN, PAN, Mesh, or other suitable network. The network communication between the system components 102, 104, 106, 108, 110, 112, 125, 140, and 150, can be encrypted using PGP, Blowfish, AES, 3DES, HTTPS, or other suitable encryption. The network communication can occur via application programming interface (API), health level 7 (HL7) standard, ANSI-X12, Ethernet, Fiber, PCI, PCIe, InfiniBand, Wi-Fi, Bluetooth, or other suitable communication protocol.

Figure 2:
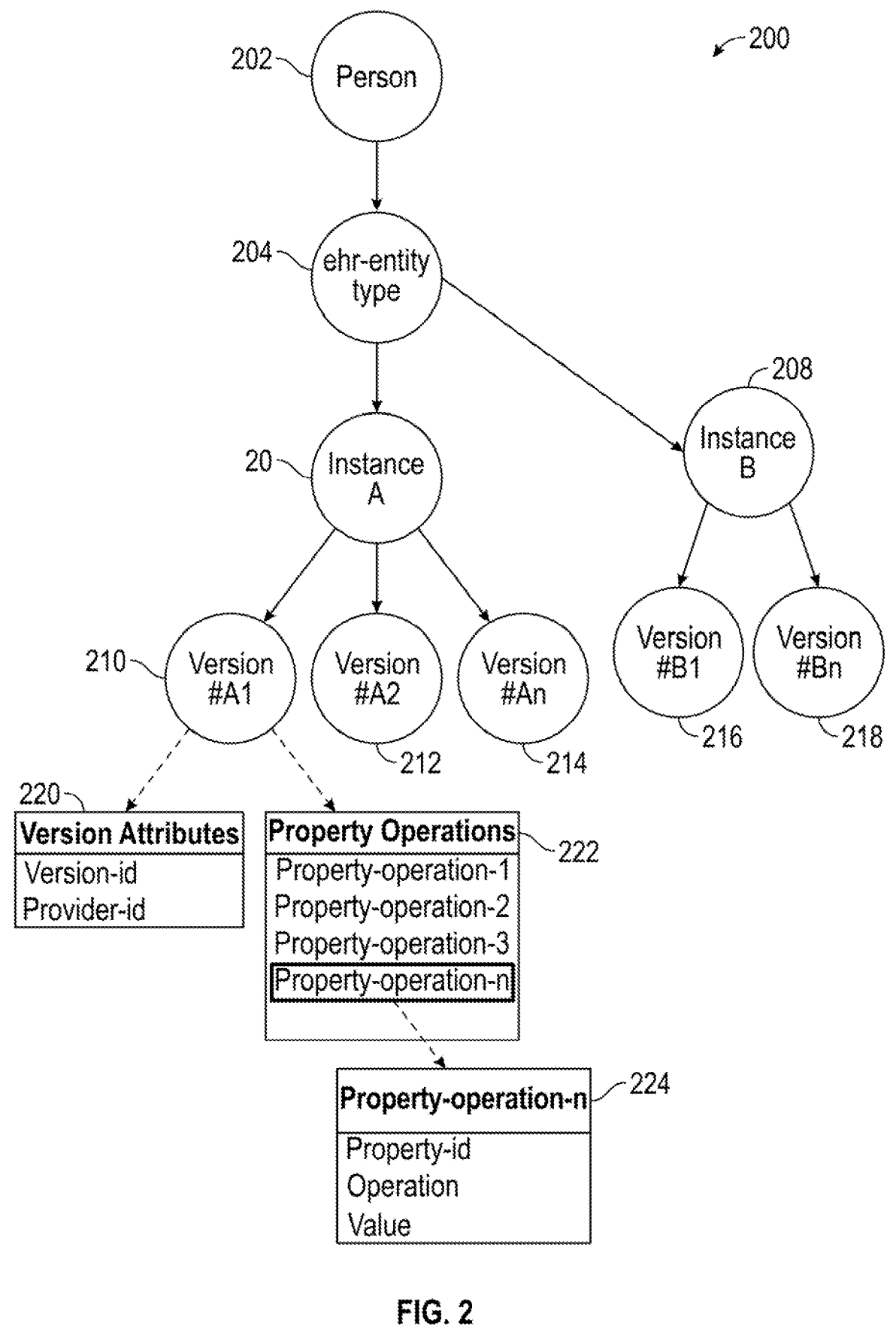

FIG. 2 illustrates a schematic view of a node hierarchy of a Global Person Record (GPR) 200, in accordance with one or more exemplary embodiments of the present disclosure. In one exemplary embodiment, the GPR can be a database of records for a plurality of persons. In another exemplary embodiment, the GPR can be stored in memory, on a blockchain, or other distributed ledger. In another exemplary embodiment, the GPR can be stored in an EHR Data Utility (e.g., a cloud-based service, which can exist as multiple instances throughout the world—the instances can be kept in-sync with each other through an nChain-API, a Bitcoin-SV Blockchain, EHR-archival-node, or other suitable system).

The GPR node hierarchy can establish a framework for organizing data related to a particular person 202. In another exemplary embodiment, a person 202 can have a record in the GPR database that is identifiable via a unique identifier for the person (person-id). For example, the unique identifier can be an alpha-numeric text string, a name, or other suitable unique identifier. In another exemplary embodiment, the person 202 can be a wrapper at the top of the hierarchy and can encompass the attributes, fields, and values related thereto. In another exemplary embodiment, the hierarchy can contain an unlimited number of grouping nodes and nodes. In another exemplary embodiment, the grouping nodes and nodes can represent different data categories. The grouping nodes and nodes can represent a collection of an ehr-entity-type 204 with one or more instance-nodes 206, 208 and one or more associated version-nodes 210, 212, 214 associated with a first instance A 206 and one or more associated version-nodes 216, 218 associated with a second instance B 208. In another exemplary embodiment, an ehr-entity-type can be a specific type of data within the GPR, such as Name, Address, etc. The hierarchy can be expanded to include a plurality of instances having a plurality of versions. In another exemplary embodiment, the ehr-entity-type 204, instance 206, and versions 210, 212, 214 can be arranged in a hierarchy.

In one exemplary embodiment, when an instance of an EHR-entity-type 204 is added to a GPR, an instance-node 206 can be created to represent the instance. In another exemplary embodiment, the ID of the instance-node 206 can be a Universally Unique IDentifier (UUID). In another exemplary embodiment, the UUID can be assigned by the client device. By using a UUID, the PUT operation can operate in a distributed environment as the ID of the instance node does not need to be dispensed by a central authority. In another exemplary embodiment, the UUID can be defined as a 128-bit integer (e.g., 0507B3EB-D817-4F27-BBC1-C29B94A155B2). In another exemplary embodiment, the UUID can be supplied by a data-provider. In another exemplary embodiment, the data-provider can be a client of the EPO-API, which can perform PUT operations to create, update, and/or delete data within the GPR. Based on the ehr-entity-type 204, the instance-node 206 will be created under the specific ehr-entity-type node 204 (e.g., Name, Address, Contact Point, etc.). A version-node 210 can also be created and referenced by the instance-node 206. The ID of the version node can be supplied by the data-provider. In another exemplary embodiment, the ID of the version node can be a UTC timestamp. For example, the timestamp can be an EPODataTimestamp (e.g. 20201019154322123). The Timestamp can facilitate the ordering of the version nodes 210, 212, 214.

In one exemplary embodiment, the version-node 210 can contain a collection of property operations 222 (e.g., operations that affect a property-collection). In another exemplary embodiment, the property operations 222, when executed, can create property-id/property-value pairs that can represent the current data values for the entity instance 206 at a specific point in time. In another exemplary embodiment, the version-node 210 can also contain a provider-id that can reference the data provider that supplied the property operations 222. In another exemplary embodiment, when properties for an instance are added, updated, or deleted, a new version-node 212 can be created and referenced by the instance-node 206. The new version-node can contain property operations which add new properties, modify existing properties, or delete existing properties defined by property-operations within the previous version-nodes. In another exemplary embodiment, the current data values for an instance can be determined by processing the property-operations for each version-node in sequential order by version ID (e.g., EPODateTimestamp). The resulting ephemeral property-collection can represent the current data items for the instance. In another exemplary embodiment, the property-collection may only exist in cache, can be created on demand, and may never be written to a database or the blockchain. The concept of an instance that supports multiple versions and property-operations within those versions is the mechanism that facilitates the process of tracking data-provider contributions.

In one exemplary embodiment, the system can implement the property-operation values identified in the following table:

| property-operation | Description |
|---|---|
| ADD | An ADD operation adds a new property-id and property-value to the property collection of the instance. |
| UPDATE | An UPDATE operation updates a property-value (e.g., which was previously added by an ADD operation within a previous version) within the property collection of the instance. |
| DELETE | A DELETE operation deletes an existing property (e.g., which was previously added by an ADD operation or updated by an UPDATE operation within a previous version) within the property collection of the instance. |

PROPERTY OPERATION EXAMPLES

Assuming the Following Properties:

| property-id | property-name |
|---|---|
| 0 | First Name |
| 1 | Middle Name |
| 2 | Last Name |
| 3 | Gender |
| 4 | Date of Birth |
| 5 | Title |

Version-0:

| provider-id = 0 | | |
|---|---|---|
| property-id | property-value | property-operation |
| 0 | John | ADD |
| 2 | Dow | ADD |
| 3 | Male | ADD |
| 4 | 19561101 | ADD |
| 5 | Mr. | ADD |

Current Property-Id/Property-Value Collection of the Instance:

| property-id | property-value |
|---|---|
| 0 | John |
| 2 | Dow |
| 3 | Male |

-continued

| property-id | property-value |
|---|---|
| 4 | 19561101 |
| 5 | Mr. |

Version-1:

| provider-id = 1 | | |
|---|---|---|
| property-id | property-value | property-operation |
| 1 | Frank | ADD |
| 2 | Doe | UPDATE |

Current Property-Id/Property-Value Collection of the Instance:

| property-id | property-value |
|---|---|
| 0 | John |
| 1 | Frank |
| 2 | Doe |
| 3 | Male |
| 4 | 19561101 |
| 5 | Mr. |

Version-2:

| provider-id = 0 | | |
|---|---|---|
| property-id | property-value | property-operation |
| 5 | | DELETE |

Current Property Id/Value Collection of the Instance:

| property-id | property-value |
|---|---|
| 0 | John |
| 1 | Frank |
| 2 | Doe |
| 3 | Male |
| 4 | 19561101 |

In operation, in one exemplary embodiment, the EHR-data-utility having servers, processors, machine readable instructions, and memory, can select a person from directory/table having a list of names, or receive a name along with a data request received from a client over a network. In another exemplary embodiment, in time order, the system can generate a property collection for a person, within the person's hierarchy, and a timestamp of the property collection generation. The system can open the first property collection created by, for example, Pharmacy 1. Additional property collections can be nodes that exist as different instances (e.g., Instance A 206, Instance B 208, to Instance n) or different versions (e.g., Version #A1 210, Version #A2 212, to Version #An 214) for a particular person with the different nodes being data received from hospitals, insurance companies, laboratories, etc. In one exemplary embodiment, the Version nodes can include one or more version attributes 220 or property operations 222. The property operations 222 can further have property-operation-attributes 224 (e.g., property-id, operation, value, etc.). All the property collections for a person may have the same or different data. Many times, the data may have only a few common entries, such as name and address, among others.

The EHR Data Utility can generate an empty property collection and add a first name, using the aforementioned property-operations, from a request for data that was received from a requestor. In one exemplary embodiment, the EHR Data Utility can identify that a person's last name is missing from the property collection created from the request, and can add, via one or more processors, a last name from one of the other property collections for a particular person. In another exemplary embodiment, the property collection can have a typo in the first name and the system can identify differences in the first name field. For example, one or more processors can execute a difference command, or correlate the ASCII values between the two fields, or hash the fields (or a portion thereof) and determine the differences, or other suitable operation to determine differences. In another exemplary embodiment, the EHR Data Utility can correlate a field of a property collection across multiple timestamps to identify the correct first name and can overwrite the first name field in the property collection with a typo to correct the typo. For example, the EHR Data Utility can conduct a statistical analysis (e.g., average, mean, median, etc.) of the values of the field over multiple time entries to identify the correct field value. In another exemplary embodiment, the EHR Data Utility can automatically attempt to retrieve data relevant to a particular request. Advantageously, the end result of these operations (to the extent the data is available) is that validated data is returned to a data-consumer, such that any missing information is provided and any erroneous information is corrected.

In one exemplary embodiment, the EHR Data Utility can build a history through these commands and can create a property collection for any moment in time, with a timestamp added as metadata to the collection. Better yet, the provider that provides the missing data can be annotated with the property operation such that an audit trail can be created for verification or monetization purposes. By using timestamps for each property collection, information for a person for a particular date can be identified and retrieved. If data is errantly changed, the data just prior to the errant data change can be repopulated. In another exemplary embodiment, the EHR Data Utility can effectively track, on a field-by-field basis, who contributed data for a particular property collection. So, for any moment in time, the EHR Data Utility can identify the contribution and identify who provided it.

Figure 3:
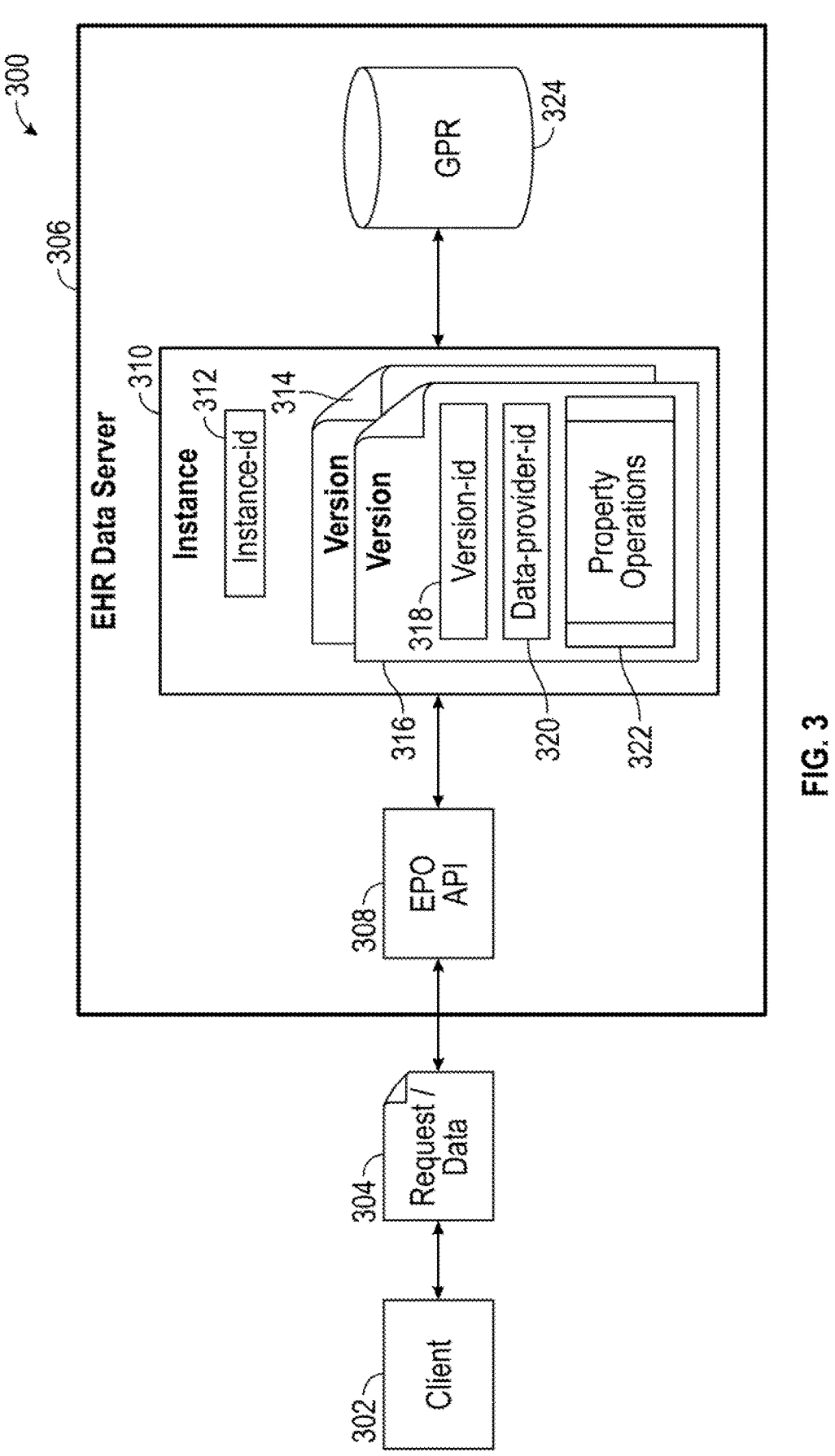
FIG. 3 illustrates a schematic view of a data transfer architecture, in accordance with one or more exemplary embodiments of the present disclosure.

FIG. 3 illustrates a schematic view of a data transfer architecture, in accordance with one or more exemplary embodiments of the present disclosure. A property collection generation system can include a client device 302, an ehr-data-utility (EHR Data Server) 306, an EPO-API 308, an instance module 310, and a GPR database 324, among others.

The aforementioned system components, and their sub-components, can be communicably coupled to each other via the Internet, intranet, or other suitable network. The communication can be encrypted, unencrypted, over a VPN tunnel, or other suitable communication means. The Internet can be a WAN, LAN, PAN, Mesh, or other suitable network. The network communication between the system components, and their sub-components, can be encrypted using PGP, Blowfish, Twofish, AES, 3DES, HTTPS, or other suitable encryption. The network communication can occur via application programming interface (API), NCPDP tele-communications standard, NCPDP-Script, FHIR, ANSI- X12, CPhA, HL7, Ethernet, Wi-Fi, Bluetooth, PCI, PCI-Express, Fiber, or other suitable communication protocol, standard, or medium.

In one exemplary embodiment, the ehr-data-utility 306 can be a server. In another exemplary embodiment, the ehr-data-utility 306 can instantiate various modules of the server. In another exemplary embodiment, the ehr-data-utility 306 can be distributed across multiple servers, processors, appliances, or devices. In one exemplary embodiment, the system can provide access to internal and external databases and distributed ledgers. For example, platform services can incorporate modules that can be integrated to existing enterprise IT infrastructure to provide additional functionality (e.g., nChain® enterprise-grade blockchain solutions, Ethereum® blockchain solutions, and the like).

In one exemplary embodiment, the ehr-data-utility 306 can receive and transmit data to a client device 302. In another exemplary embodiment, a client device 302 can transmit a request or data 304 to the ehr-data-utility 306. The client device 302 can be external to the ehr-data-utility 306, but operably coupled to the server 306 via a network. The client device 302 can be a data-provider (e.g., a client that can perform PUT operations to create, update, and/or delete data within the GPR database 324) or a data-consumer (e.g., a client that can perform GET operations to consume data from the GPR database 324). The request or data 304 transmitted by the client 302 can be received by the ehr-data-utility 306 via the EPO-API 308.

The EPO-API 308 (EHR Data Permissioned Operations Application Programming Interface) can be used by data providers and data consumers to interact with the ehr-data-utility 306. In one exemplary embodiment, the EPO-API 308 can be used to interact with a person's particular GPR. The GPR database 324 can be stored in memory internal or external to the ehr-data-utility 306. The EPO-API 308 can support GET and PUT operations for data within a GPR database 324, EPO database, third-party database, or other suitable database.

In one exemplary embodiment, each data operation can result in the generation of a property-operation for one or more data-items. Every data-provider can have a unique ID known as a data-provider-id 320. In another exemplary embodiment, the data-provider-id 320 can be a static ID that never changes or a dynamic identifier that changes based on the session. In another exemplary embodiment, since a variety of data-providers can contribute to specific instances of data within the GPR database 324, the ehr-data-utility 306 can track the data contributions by writing the property-operations 322 and the data-provider-id 320 to the GPR. In general, an instance 310 of an ehr-entity-type can have multiple data items. In another exemplary embodiment, these data items can be represented as an ephemeral property-collection. Creation of, and changes to, the property-collection can be made by a collection of property-operations 322. These property-operations 322, along with the provider-id 320 of the data-provider can be written to a time stamped version-node 316 by the ehr-data-utility 306. This data can be written as fields of the version-node or appended as metadata. In another exemplary embodiment, over time, a variety of data-providers can contribute to the instance 310 data. In another exemplary embodiment, an instance 310 can include multiple versions 314, 316, with one or more property-operations 322 within those versions to facilitate the tracking of data-provider contributions.

In one exemplary embodiment, the ehr-data-utility 306 can operably communicate with currency exchange systems, such as cryptocurrency (e.g., Bitcoin®), ACH services, banking services, wire transfer services, and other relevant currency exchange systems.

Figure 4:
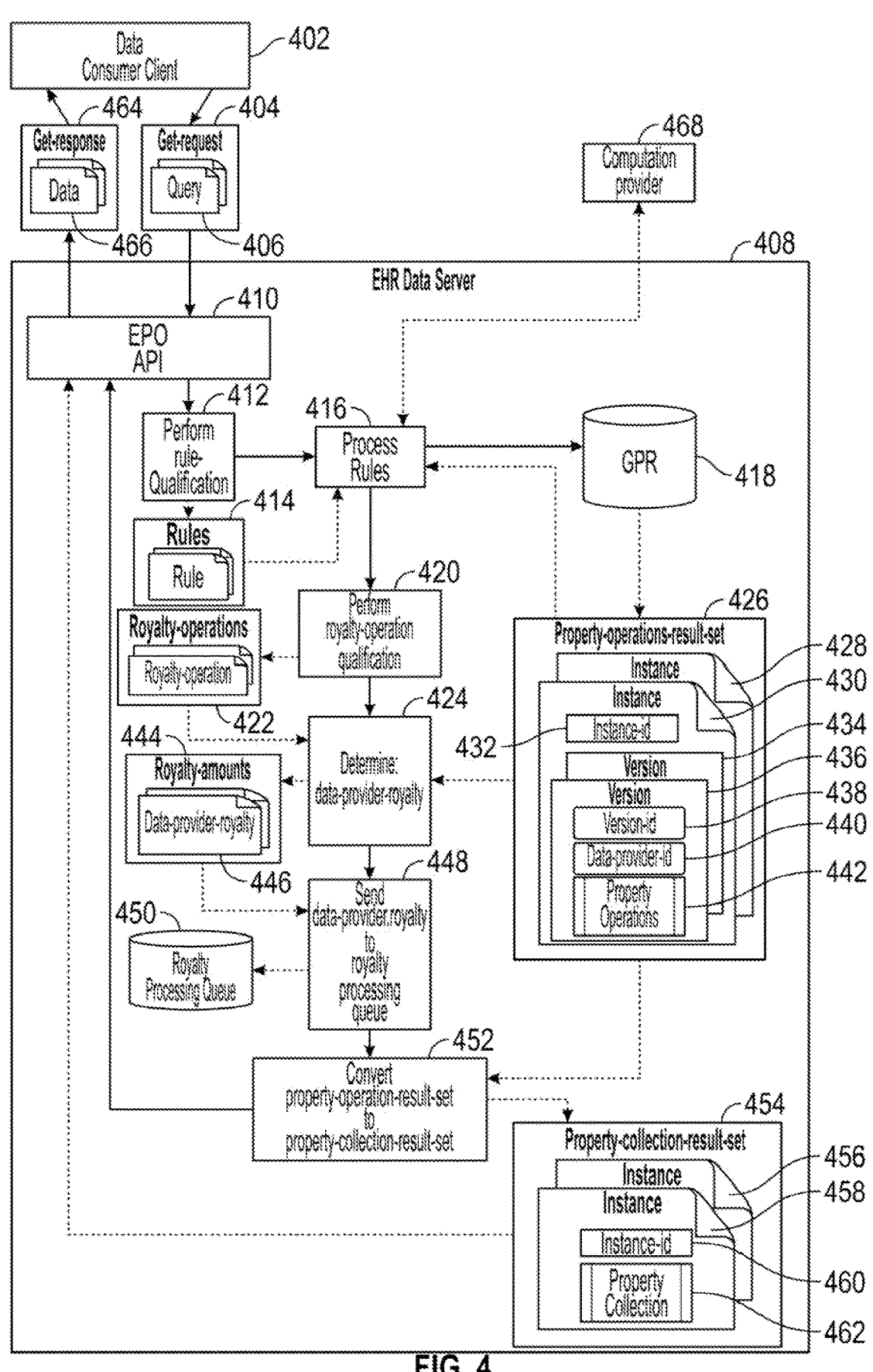
FIG. 4 illustrates a flowchart diagram exemplifying control logic embodying features of a method of executing a GET operation, in accordance with one or more exemplary embodiments of the present disclosure.

FIG. 4 illustrates a flowchart diagram exemplifying control logic embodying features of a method of executing a GET operation, in accordance with one or more exemplary embodiments of the present disclosure. The GET operation control logic 400 can be implemented as an algorithm on a processor, a server, a machine learning module, or other suitable system. The GET operation control logic 400 can be achieved via software, hardware, an application programming interface (API), a network connection, a network transfer protocol, HTML, DHTML, JavaScript, Dojo, Ruby, Rails, other suitable applications, or a suitable combination thereof.

The GET operation control logic 400 can leverage the ability of a computer platform to spawn multiple processes and threads by processing data simultaneously. The speed and efficiency of the GET operation control logic 400 can be greatly improved by instantiating more than one process. However, one skilled in the art of programming will appreciate that use of a single processing thread may also be utilized and is within the scope of the present disclosure. In one exemplary embodiment, the GET operation control logic 400 can instantiate various modules of the server. In another exemplary embodiment, the GET operation control logic 400 can be distributed across multiple servers, processors, appliances, or devices.

In one exemplary embodiment, the GET operation control logic 400 can utilize EPO-API 410 to GET data from the GPR database 418. When the EPO-API 410 is used to retrieve data, the operation is known as a GET operation. In another exemplary embodiment, the GET operation control logic 400 can retrieve a variety of ehr-entity-type data instances 428, 430. For large data items (e.g., videos, images, etc.), the data can be streamed to the data consumer client 402. Whenever the GET operation control logic 400 retrieves data, the data can be monetized by tracking the property-operations and data-providers. In another exemplary embodiment, the GET operation control logic 400 can calculate a royalty for the parties (e.g., person, data-providers, ehr-data-utility provider, etc.) involved in the GET operation. In another exemplary embodiment, during an EPO-API 410 GET operation, the app-id and data-provider-id 440 can be used when processing the request. In one exemplary embodiment, a GET operation can result in the following fees: an ehr-data-utility transmission fee for performing the GET operation; and a data royalty fee for payment to all data providers that contributed the data associated with the data being retrieved, and the person that owns the data, among others. Not all operations may result in a data royalty fee. For example, the client may be the person that owns the data, or other relevant conditions. The GET operation can be monetized by determining a royalty amount based on a number of factors (royalty schemes).

In one exemplary embodiment, a data consumer client can submit a GET-request 404 to the EPO-API 410. The GET operation control logic 400 can route the GET-request 404 to the EPO-API 410. In another exemplary embodiment, the data-consumer can submit the GET-request via a client device 402 (e.g., desktop, laptop, server, mobile device, etc.). The GET-request 404 can be transmitted to the ehr-data-utility (EHR Data Server) 408 over an encrypted network. In another exemplary embodiment, the GET-request 404 can include a query 406. The query 406 can include a request for certain data related to a particular person. The query 406 can include one or more data fields or parameters.

In one exemplary embodiment, the GET operation control logic 400 can receive the request 404. In another exemplary embodiment, the request 404 can be received by the EPO-API 410. In another exemplary embodiment, the GET operation control logic 400 can determine the app-id of the client or client device 402 making the request 404. The app-id can be a code assigned to an application developer, which can be used when submitting requests to the EPO-API 410 from a specific application. The app-id can define a predefined set of permission scopes that can be allowed by the application. A permission-scope can include a Global Property Path (GPP) and can be used to define access permissions for specific data within a GPR database 418. The GPP can be an address to an ehr-node, ehr-entity-type, ehr-entity-instance 428, or property within an ehr-entity-instance 428. The GPP can be relative to a specific type of entity such as a 'Person,' 'Patient,' Prescriber,' etc. In another exemplary embodiment, an app-id that represents a user-interface has read/write permission for all data, which can be entered by a person. In another exemplary embodiment, the GET operation control logic 400 can determine the data-provider-id 440 of the data-consumer (requestor). The data-provider-id 440 can be a code assigned to a data provider, which can be used when submitting data to the GET operation control logic 400 or EPO-API 410 from a specific application. The data-provider-id 440 can define a predefined set of permission scopes that can be allowed for the specific provider. The predefined set of permission scopes can provide a security mechanism to control which operations are allowable for a particular client, provider-id, data type, or other relevant parameter. In another exemplary embodiment, the GET operation control logic 400 can determine the person-id associated with the request. For example, the request can include a person-id for a particular person related to the request. In one exemplary embodiment, the control logic 400 can pass the GET-request 404 to a Transmission Processing Engine (TPE). In another exemplary embodiment, the TPE can perform rule qualification 412. In another exemplary embodiment, rule-qualification 412 can determine the rules 414 and the associated rule-properties to be used when processing a request 404. In one exemplary embodiment, a rule 414 can include compiled computer code, smart contract, or other instruction that can be used to process a request. Rules 414 can be processed sequentially and in order of priority, or other predetermined or use-selectable scheme. In another exemplary embodiment, rule-properties can be a property collection that can be used as one or more parameters for a rule. In another exemplary embodiment, the TPE rule qualification process 412 can determine which rules should be run based on: request message contents, configuration settings, connection properties, app-id, provider-id, or any addressable attribute, among other relevant metrics.

In one exemplary embodiment, at 416, the qualified rules can be processed by the control logic 400. In another exemplary embodiment, the control logic 400 can instantiate the TPE to process the rules. In another exemplary embodiment, the control logic 400 can process at least one rule to search the GPR database 418 to retrieve a property-operation-result-set 426 for the ehr-entity-type(s) of interest. For example, the property-operation-result-set 426 can include one or more instances 428, 430. Each instance 428, 430 can include an instance-id 432. Each instance can include one or more versions 434, 436, with each version including a version-id 438, data-provider-id 440, and one or more property operations 442. In another exemplary embodiment, rules 414 can also act as computation-providers 468, since a rule 414 can add additional data to a GET operation. In another exemplary embodiment, a computation-provider 468 can be an entity that supplies data computation services via one or more specialized algorithms. The specialized algorithm can receive data from the control logic 400, analyze the data, and return a data result, which can be provided to a data-consumer. In another exemplary embodiment, computation can be monetized using the same model that is used for data monetization. In another exemplary embodiment, the computation-provider 468 can be a third-party that is operatively coupled to the control logic 400 via a network. In another exemplary embodiment, the computation-provider could provide an annotation of a single instance of data or a group of data. For example, a Google® AI can analyze a radiology image or group of images to determine if a tumor is present and annotate the location of the tumor in the image. In another exemplary embodiment, the computation-provider 468 could provide a calculation associated with a single instance of data or a group of related data. For example, a Morphine Milligram Equivalent (MME) edit that can determine an MME value for a single drug or a group of drugs (e.g., opioids on a person's prescription profile).

In one exemplary embodiment, the control logic 400 can perform royalty-operation qualification 420, which can return a result set of royalty-operations 422. In another exemplary embodiment, the control logic 400 can instantiate the TPE to perform royalty-operation qualification 420. In another exemplary embodiment, a royalty-operation 422 can include predefined computer logic used to calculate a royalty for each data-provider-id 440 in a property-operations-result-set 426. The control logic 400 can determine which royalty-operations 422 qualify based on: configuration settings, request message contents, connection properties, app-id, data-provider-id 440, or any addressable attribute, among others.

In one exemplary embodiment, at 424, for each royalty-operation, a data-provider-royalty will be determined by the control logic 400. In another exemplary embodiment, a royalty percentage of a specific amount can be determined by the control logic 400 for the property-operations. The royalty amount 444 can be determined by the control logic 400 based upon the cost of the service, cost of the data transfer, or other relevant metric. The royalty amount 444 can then be divided amongst the parties (including the patient), such that each contributor can receive a portion of the royalty, so each party related to the transaction gets rewarded for their contribution. The royalty amounts 444 can include a data-provider-royalty 446, a patient royalty, and an ehr-data-utility provider royalty. The degree that each contributing party gets rewarded can be an equal percentage (dividing the royalty by the number of parties involved in the transaction), weighted, such that the remaining parties to the transaction split the remainder based on a weighted multiplier (discussed below), or other suitable distribution.

In one exemplary embodiment, at 448, the control logic 400 can transmit each data-provider-royalty to a data-provider-royalty processing queue 450. In another exemplary embodiment, the control logic 400 can effect the transfer of data and payment of royalties and processing fees. In another exemplary embodiment, the control logic can effect the payment of royalties and fees via a smart contract on a blockchain. In another exemplary embodiment, platform services can include an API that can create a digital/crypto currency transaction directly on a blockchain currency exchange, such as the Bitcoin SV blockchain. The transaction on the Bitcoin SV blockchain can transfer the identified number of tokens from the data-consumer account to each data-provider's account, utility, and person. In another exemplary embodiment, the currency exchange can be via credit or debit card transfer. In another exemplary embodiment, the payment can be effectuated via bank-to-bank transfer, or other suitable form of payment. The control logic 400 provides the technological advantage of providing a single source of truth and the rewarding people or companies for the use of their data.

In one exemplary embodiment, at 452, the control logic 400 can convert the property-operation-result-set 426 to a property-collection-result-set 454. In another exemplary embodiment, the property-collection-result-set 454 can include the patient data responsive to the request 404. In another exemplary embodiment, the property-collection-result-set 454 can include one or more instances 456, 458. Each instance can include an instance-id 460 and a property collection 462. In one exemplary embodiment, the control logic 400 can pass control of the process back to the EPO-API, which can send the property-collection-result-set 454 to the data-consumer-client 402. In another exemplary embodiment, the property-collection-result-set 454 can be transmitted to the data-consumer-client 402 via a get-response 464 having data 466, such as the property-collection-result-set 454, among other relevant data. The control logic 400 can then terminate or await a new get-request 404 and can repeat the aforementioned steps.

Figure 5:
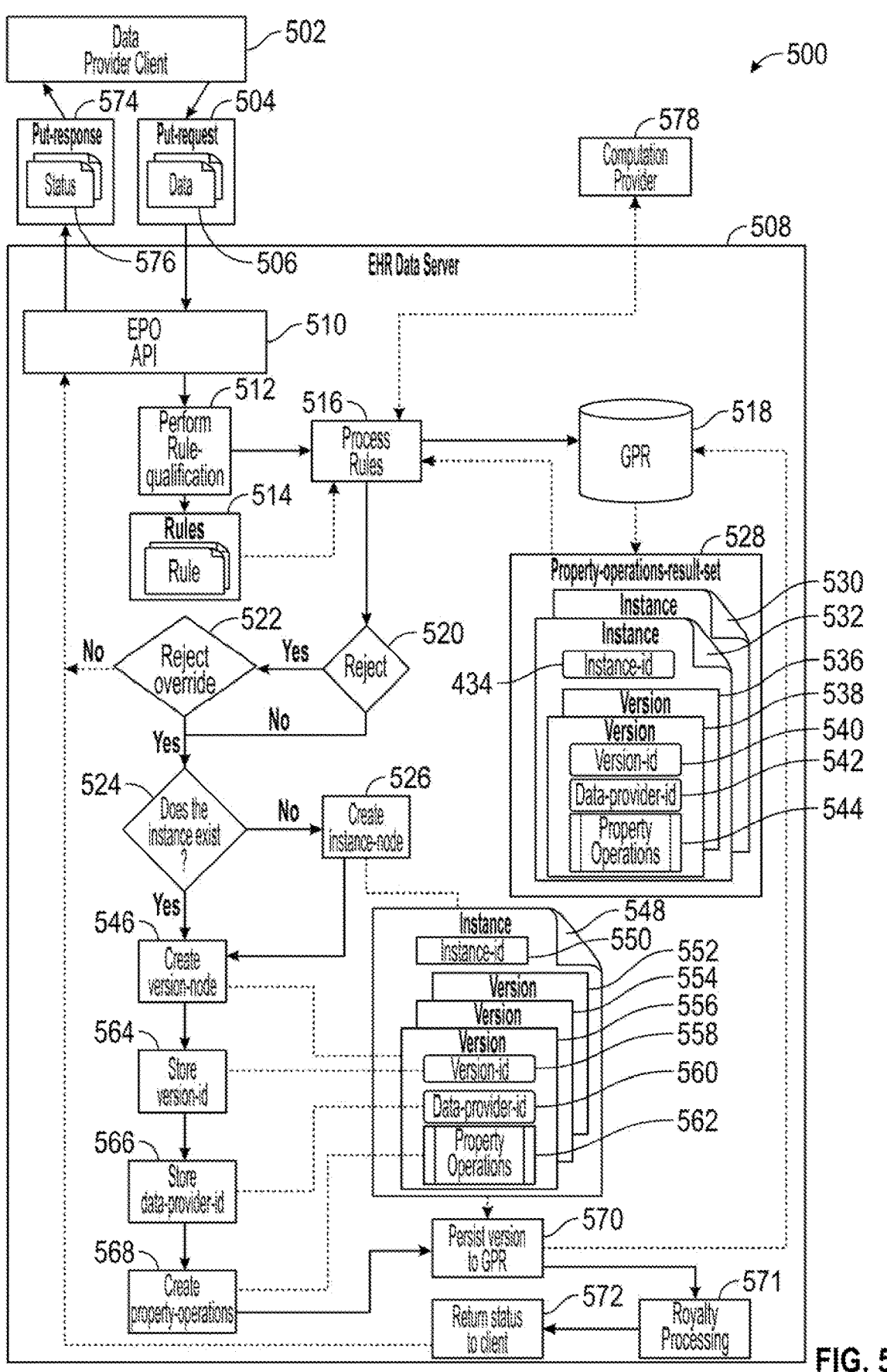
FIG. 5 illustrates a flowchart diagram exemplifying control logic embodying features of a method of executing a PUT operation, in accordance with one or more exemplary embodiments of the present disclosure.

FIG. 5 illustrates a flowchart diagram exemplifying control logic embodying features of a method of executing a PUT operation, in accordance with one or more exemplary embodiments of the present disclosure. The PUT operation control logic 500 can be implemented as an algorithm on a processor, a server, a machine learning module, or other suitable system. The PUT operation control logic 500 can be achieved via software, hardware, an application programming interface (API), a network connection, a network transfer protocol, HTML, DHTML, JavaScript, Dojo, Ruby, Rails, other suitable applications, or a suitable combination thereof.

The PUT operation control logic 500 can leverage the ability of a computer platform to spawn multiple processes and threads by processing data simultaneously. The speed and efficiency of the PUT operation control logic can be greatly improved by instantiating more than one process. However, one skilled in the art of programming will appreciate that use of a single processing thread may also be utilized and is within the scope of the present disclosure. In one exemplary embodiment, the PUT operation control logic can instantiate various modules of the server. In another exemplary embodiment, the PUT operation control logic 500 can be distributed across multiple servers, processors, appliances, or devices.

In one exemplary embodiment, the EPO-API 510 can be used to transmit data in the GPR database 518. In another exemplary embodiment, a PUT operation can be used to insert data into the GPR database 518. In another exemplary embodiment, during an EPO-API 510 PUT operation, the app-id and data-provider-id 542 can be used when processing a put-request 504. The data-provider-id 542 can be stored with new data added to the GPR database 518. If the data is later monetized, the data provider can receive a data royalty for the data. In another exemplary embodiment, a PUT operation may not be subject to any fees. For large data items (e.g., videos, images, etc.), the data can be streamed from the data-provider-client 502. Whenever data is provided, the data can be monetized by tracking the property-operations 544 and data-providers. In another exemplary embodiment, the PUT operation control logic 500 can calculate a royalty for the parties (e.g., person, data-providers, ehr-data-utility provider, etc.) involved in the PUT operation. The PUT operation can be monetized by determining a royalty amount based on a number of factors (royalty schemes).

In one exemplary embodiment, a data-provider client can perform a PUT operation. In another exemplary embodiment, the data-provider can submit a PUT-request 504 via a data provider client device 502 (e.g., desktop, laptop, server, mobile device, etc.). The PUT-request 504 can be transmitted to the ehr-data-utility (EHR Data Server) 508 over an encrypted network. In another exemplary embodiment, the PUT-request 504 can include data 506 related to a particular person. The PUT-request 504 can include one or more data fields or parameters.

In one exemplary embodiment, the PUT operation control logic 500 can receive the data 506 within the PUT request 504. In another exemplary embodiment, the data 506 can be received by the EPO-API 510. In another exemplary embodiment, the PUT operation control logic 500 can determine the data-provider-id 542 of the provider making the request. The data-provider-id 542 can be a code assigned to a data-provider, which can be used when transmitting data to the EPO-API 510 from a client 502. The data-provider-id 542 can have a predefined set of permission scopes that can be allowed by the application associated with it. The predefined set of permission scopes can provide a security mechanism to control which operations are allowable for a particular client, provider-id, data type, or other relevant parameter.

In one exemplary embodiment, the control logic 500 can transmit the PUT-request 504 to a Transmission Processing Engine (TPE). In another exemplary embodiment, the TPE can perform rule qualification 512. In another exemplary embodiment, rule-qualification 512 can determine the process of determining the rules 514 and the associated rule-properties to be used when processing a request 504. In one exemplary embodiment, a rule 514 can include compiled computer code, smart contract, or other instruction that can be used to process a request 504. Rules 514 can be processed sequentially and in order of priority, or other predetermined or use-selectable scheme. In another exemplary embodiment, rule-properties can be a property collection that can be used as one or more parameters for a rule 514, when a rule 514 has been executed to process a request 504. In another exemplary embodiment, the TPE rule qualification process 512 can determine which rules 514 should be run based on: request message contents, configuration settings, connection properties, app-id, data-provider-id 542, or any addressable attribute, among other relevant metrics.

In one exemplary embodiment, at 516, the control logic 500 can instantiate the TPE to process those rules 514 that qualified. The rules 514 can perform tasks such as: validate the data items; execute algorithms against data (computation-provider) to provide additional information about the data; locate the associated person within the GPR database 518; locate the associated ehr-entity-type node, for the person, within the GPR database 518; and retrieve all the instances 530, 532 for the associated ehr-entity-type.

In one exemplary embodiment, at 520, the control logic 500 can determine whether the data already exists within an existing instance. If so, the TPE can set a rejection flag or provide some other suitable notification. If not, at 524 the control logic 500 can determine whether instance-node exists. In one exemplary embodiment, at 522, the control logic 500 can determine whether the PUT-operation includes a reject-override. If not, a status is returned to the client 502 indicating that the PUT-operation has been rejected because the data already exists. If so, at 524, the control logic 500 can determine whether instance-node exists.

In one exemplary embodiment, if the instance-node does not exist, an instance-node can be created at 526 by the control logic 500 and the UUID provided by the data-provider can be stored in the instance-node 548 as the instance-id attribute 550. Each instance 428, 430 can include an instance-id 432. The instance 548 can include one or more versions 552, 554, 556, with each version including a version-id 558, data-provider-id 560, and one or more property operations 562. In another exemplary embodiment, the control logic 500 can generate the version-node 546. The version-id 558 provided by the data-provider can be stored in the version-node 556 as the version-id attribute 558, and the data-provider-id 560 can be stored in the version-node 556 as an attribute.

In one exemplary embodiment, at 568, the control logic 500 can create property operations by converting the data-items to property-operations 562 and store them as a collection within the version-node 556. In another exemplary embodiment, at 570, the version-node 556 can be persisted (e.g., written) to the GPR database 518.

In one exemplary embodiment, at 571, the control logic 500 can initiate and perform royalty processing. The royalty processing can be conducted as disclosed in FIG. 4. In one exemplary embodiment, the control logic 500 can perform royalty-operation qualification, as in step 420, which can return a result set of royalty-operations, as in step 422. In another exemplary embodiment, the control logic 500 can instantiate the TPE to perform royalty-operation qualification, as in step 420. In another exemplary embodiment, a royalty-operation, as in step 422, can include predefined computer logic used to calculate a royalty for each data-provider-id, as in step 440, in a property-operations-result-set, as in step 426. The control logic 500 can determine which royalty-operations, as in step 422, qualify based on: configuration settings, request message contents, connection properties, app-id, data-provider-id, or any addressable attribute, among others.

In one exemplary embodiment, as in step 424, for each royalty-operation, a data-provider-royalty will be determined by the control logic 500. In another exemplary embodiment, a royalty percentage of a specific amount can be determined by the control logic 500 for the property-operations. The royalty amount, as in step 444, can be determined by the control logic 500 based upon the cost of the service, cost of the data transfer, or other relevant metric. The royalty amount, as in step 444, can then be divided amongst the parties (including the patient), such that each contributor can receive a portion of the royalty, so each party related to the transaction gets rewarded for their contribution. The royalty amounts, as in step 444, can include a data-provider-royalty, as in step 446, a patient royalty, and an ehr-data-utility provider royalty. The degree that each contributing party gets rewarded can be an equal percentage (dividing the royalty by the number of parties involved in the transaction), weighted, such that the remaining parties to the transaction split the remainder based on a weighted multiplier (discussed below), or other suitable distribution.

In one exemplary embodiment, as in step 448, the control logic 500 can transmit each data-provider-royalty to a data-provider-royalty processing queue, as in step 450. In another exemplary embodiment, the control logic 500 can effect the transfer of data and payment of royalties and processing fees. In another exemplary embodiment, the control logic can effect the payment of royalties and fees via a smart contract on a blockchain. In another exemplary embodiment, platform services can include an API that can create a digital/crypto currency transaction directly on a blockchain currency exchange, such as the Bitcoin SV blockchain. The transaction on the Bitcoin SV blockchain can transfer the identified number of tokens from the data-consumer account to each data-provider's account, utility, and person. In another exemplary embodiment, the currency exchange can be via credit or debit card transfer. In another exemplary embodiment, the payment can be effectuated via bank-to-bank transfer, or other suitable form of payment. The control logic 500 provides the technological advantage of providing a single source of truth and the rewarding people or companies for the use of their data.

In another exemplary embodiment, at 572, the results can be returned to the data-provider client by the control logic 500 via the EPO-API 510. The EPO-API 510 can then transmit a put-response 574 to having a status 576 to the data provider client 502. The control logic 500 can then terminate or await a new put-request 504 and can repeat the aforementioned steps.

Data Monetization

In one exemplary embodiment, when data is retrieved, or additional data is provided by a computation-provider, it may be monetized by determining a royalty amount based on a number of factors (royalty schemes), which may include: the data-consumer consuming the data (payment method, volume, location, contract, etc.), the data-provider(s) that contributed the data, the ehr-entity-type(s) of data being consumed, a computation-provider result, the size of the data being consumed, the storage medium of the data being consumed, the delivery mechanism of the data being consumed, the data transformation processes, etc. Any of these factors may be considered during the monetization royalty-qualification-process. The result of the royalty-qualification-process can be a data-set that describes a royalty-operation for the data as a whole or each ehr-entity-type instance being retrieved. A royalty-operation can be: a fixed cost for all the ehr-entity-type instances being retrieved; a fixed cost for each ehr-entity-type instance being retrieved; a variable cost based on the total byte count of the data being retrieved; a variable cost based on the byte count for each ehr-entity-type instance being retrieved; a cost based on the byte count for each ehr-entity-type instance being retrieved, a weighting factor for each ehr-entity-type, and the total byte count of the data being retrieved; a fixed cost based on an algorithm that can be dynamically added to the system; or a variable cost based on an algorithm that can be dynamically added to the system.

Data Monetization Royalty Ratio Calculation Example

As an example, a royalty-operation that is based on byte counts, are based on the byte counts contributed by each data-provider. For each data-provider a royalty-ratio is determined by dividing the byte count for a property operation by the total bytes of data for the instance. For the instance defined above, the royalty ratios for each data provider would be determined as follows:

| property-id | bytes | provider-id | royalty ratio |
|---|---|---|---|
| 0 | 4 | 0 | 4/20 |
| 1 | 5 | 1 | 5/20 |
| 2 | 3 | 0 | 3/20 |
| 3 | 4 | 0 | 4/20 |
| 4 | 4 | 0 | 4/20 |

Total Royalty Ratio by Data Provider:

| provider-id | total royalty ratio |
|---|---|
| 0 | 15/20 |
| 1 | 5/20 |

Royalty Payment Amount Example

If the royalty-operation in the above example was a fixed price royalty of $5, the royalty payments for each data-provider would be calculated as follows:

| provider-id | Royalty Ratio | Royalty Amount |
|---|---|---|
| 0 | 15/20 | $3.75 |
| 1 | 5/20 | $1.25 |

In one exemplary embodiment, the royalty calculation can be determined based upon a weighted multiplier. For example, the weighted multiplier can be based on a table that identifies the ehr-entity-type of the data consumer and determines the property collection category such that the significance of the data can be allocated based on the correlation of the entity type and the property collection category. If the entity type and the property collection category match, the significance of the data provided is high and so the weighted multiplier is higher for that data provider than the others. The difference or weights can be predetermined and user-selectable, as stored in the table. For example, if an MM service provider is requesting MRI image data, the correlation of the entity type and the property collection category would match and the weighted multiplier would be the highest in the table, because ostensibly MM image data can be significant to the MRI service provider.

Persons skilled in the art will readily understand that these advantages (as well as the advantages indicated in the summary) and objectives of this system would not be possible without the particular combination of computer hardware, control logic, and other structural components and mechanisms assembled in this inventive system and described herein. It will be further understood that a variety of programming tools, known to persons skilled in the art, are available for implementing the control of the features and operations described in the foregoing disclosure. Moreover, the particular choice of programming tool(s) may be governed by the specific objectives and constraints placed on the implementation selected for realizing the concepts set forth herein and in the appended claims.

The description in this patent document should not be read as implying that any particular element, step, or function can be an essential or critical element that must be included in the claim scope. Also, none of the claims can be intended to invoke 35 U.S.C. § 112(f) with respect to any of the appended claims or claim elements unless the exact words "means for" or "step for" are explicitly used in the particular claim, followed by a participle phrase identifying a function. Use of terms such as (but not limited to) "mechanism," "module," "device," "unit," "component," "element," "member," "apparatus," "machine," "system," "processor," "processing device," or "controller" within a claim can be understood and intended to refer to structures known to those skilled in the relevant art, as further modified or enhanced by the features of the claims themselves, and can be not intended to invoke 35 U.S.C. § 112(f).

The disclosure may be embodied in other specific forms without departing from the spirit or essential characteristics thereof. For example, each of the new structures described herein, may be modified to suit particular local variations or requirements while retaining their basic configurations or structural relationships with each other or while performing the same or similar functions described herein. The present embodiments are therefore to be considered in all respects as illustrative and not restrictive. Accordingly, the scope of the inventions can be established by the appended claims rather than by the foregoing description. All changes which come within the meaning and range of equivalency of the claims are therefore intended to be embraced therein. Further, the individual elements of the claims are not well-understood, routine, or conventional. Instead, the claims are directed to the unconventional inventive concept described in the specification.

What is claimed is:

1. A method of providing real-time patient data royalty calculation by a computing system, the computing system including one or more processors configured to execute computer program instructions, comprising:

spawning a first computer process configured to execute a first set of computer program instructions of the computer program instructions;

spawning, concurrently with the spawning of the first computer process, a second computer process configured to execute a second set of computer program instructions of the computer program instructions, wherein a combination of the first set of computer program instructions and the second set of computer program instructions is configured to perform the steps of the method of providing real-time patient data royalty calculation;

receiving a request having one or more patient data parameters from a client via an encrypted network;

generating a version node as a child of an instance node, via a utility, having one or more property operations related to a patient and a data-provider-id identifying each of one or more data providers of the one or more property operations;

organizing, via a global person record node hierarchy having a plurality of nodes, data received from the one or more data providers responsive to the request, wherein the organizing includes:

identifying, via the utility, missing data in a property collection associated with the patient and created from the request using the one or more property operations;

retrieving, via the utility, the missing data from one or more other property collections associated with the patient and created from the request using the one or more property operations;

adding, via the utility, the retrieved missing data to the property collection; and annotating the property collection with a property operation identifying the data provider that provided the missing data;

tracking, via the utility, the one or more data providers, the data-provider-id of each of the one or more data providers, and the data provided, and appending meta-data identifying the origin of the provided data into one of the plurality of nodes based on the annotated property collection;

calculating, via one or more processors, fixed or variable royalties based upon data category, data size, request attributes payable to each of the one or more data providers, the utility, and the patient, based on a royalty scheme; and paying the royalty amounts to each of the one or more data providers, the utility, and the patient.

2. The method of claim 1, wherein the royalty scheme is based on characteristics of the data-consumer consuming the data.

3. The method of claim 2, wherein the characteristics include a payment method, data volume, location, contract type.

4. The method of claim 1, wherein the instance node and the version node is stored on a blockchain.

5. The method of claim 1, wherein the royalty scheme is based on, an entity type of the data being consumed.

6. The method of claim 1, wherein the royalty scheme is based on a computation-provider result.

7. The method of claim 1, wherein the royalty scheme is based on the size of the data being consumed.

8. The method of claim 1, wherein the royalty amount is calculated using an equal percentage.

9. The method of claim 1, wherein the royalty amount is calculated using a weighted percentage based on a weighted multiplier.

10. The method of claim 9, wherein the weighted multiplier is based on the correlation of an entity type and a property collection category.

11. A system for providing real-time patient data royalty calculation, comprising:

a memory storing one or more patient data parameters; and a processor operably coupled to the memory and configured to execute machine-readable instructions, wherein the configuration of the processor to execute the machine-readable instructions includes configuration to spawn a first computer process configured to execute a first set of instructions of the machine-readable instructions and to spawn a second computer process configured to execute a second set of instructions of the machine-readable instructions, wherein the first computer process and the second computer process are spawned concurrently, wherein a combination of the first set of computer program instructions and the second set of computer program instructions is configured to perform program steps comprising:

receiving a request having one or more patient data parameters from a client via an encrypted network;

generating a version node as a child of an instance node, via a utility, having one or more property operations related to a patient and a data-provider-id identifying each of one or more data providers of the one or more property operations;

organizing, via a global person record node hierarchy having a plurality of nodes, data received from the one or more data providers responsive to the request, wherein the organizing includes:

identifying, via the utility, missing data in a property collection associated with the patient and created from the request using the one or more property operations;

retrieving, via the utility, the missing data from one or more other property collections associated with the patient and created from the request using the one or more property operations;

adding, via the utility, the retrieved missing data to the property collection; and annotating the property collection with a property operation identifying the data provider that provided the missing data;

tracking, via the utility, the one or more data providers, the data-provider-id of each of the one or more data providers, and the data provided, and appending metadata identifying the origin of the provided data into one of the plurality of nodes based on the annotated property collection;

calculating, via one or more processors, fixed or variable royalties based upon data category, data size, request attributes payable to each of the one or more data providers, the utility, and the patient, based on a royalty scheme; and paying the royalty amounts to each of the one or more data providers, the utility, and the patient.

12. The system of claim 11, wherein the royalty scheme is based on characteristics of the data-consumer consuming the data.

13. The system of claim 12, wherein the characteristics include a payment method, data volume, location, contract type.

14. The system of claim 11, wherein the instance node and the version node is stored on a blockchain.

15. The system of claim 11, wherein the royalty scheme is based on, an entity type of the data being consumed.

16. The system of claim 11, wherein the royalty scheme is based on a computation-provider result.

17. The system of claim 11, wherein the royalty scheme is based on the size of the data being consumed.

18. The system of claim 11, wherein the royalty amount is calculated using an equal percentage.

19. The system of claim 11, wherein the royalty amount is calculated using a weighted percentage based on a weighted multiplier.

20. The system of claim 19, wherein the weighted multiplier is based on the correlation of an entity type and a property collection category.

* * * * *